(12) United States Patent
Mathias et al.

(10) Patent No.: US 6,387,086 B2
(45) Date of Patent: May 14, 2002

(54) BLOOD PROCESSING SET INCLUDING AN INTEGRATED BLOOD SAMPLING SYSTEM

(75) Inventors: Jean-Marie Mathias, Lillois; Jean-Claude Bernes, Faimes, both of (BE); Thomas Walter Coneys, Saint-Doulchard (FR)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/364,628

(22) Filed: Jul. 29, 1999

(51) Int. Cl.$^7$ .............................................. A61B 19/00
(52) U.S. Cl. ........................ 604/409; 604/4.01; 604/6.15
(58) Field of Search .................................. 604/403, 406, 604/407, 408, 409, 410, 411, 4.01–5.01, 6.15, 262; 206/438

(56) References Cited

U.S. PATENT DOCUMENTS

| | | |
|---|---|---|
| 2,469,641 A | 2/1949 | Kleiner |
| 3,459,572 A | 8/1969 | Nehring |
| 3,494,352 A | 2/1970 | Russo et al. |
| 3,817,240 A | 6/1974 | Ayres |
| 3,890,203 A | 6/1975 | Mehl |
| 3,931,815 A | 1/1976 | Takatsuki |
| 4,121,585 A | 10/1978 | Becker, Jr. |
| 4,140,108 A | 2/1979 | Nugent |
| 4,212,308 A | 7/1980 | Percarpio |
| 4,253,458 A | 3/1981 | Bacehowski et al. |
| 4,256,120 A | 3/1981 | Finley |
| 4,295,477 A | 10/1981 | Christinger |
| 4,296,759 A | 10/1981 | Joslin et al. |
| 4,307,731 A | 12/1981 | Kaufman |
| 4,320,769 A * | 3/1982 | Eichhorn et al. ........... 128/763 |
| 4,340,049 A | 7/1982 | Munsch |
| 4,441,951 A | 4/1984 | Christinger |
| 4,547,186 A | 10/1985 | Bartlett |
| 4,658,655 A | 4/1987 | Kanno |
| 4,763,648 A | 8/1988 | Wyatt |
| 4,865,583 A | 9/1989 | Tu |
| 4,867,172 A | 9/1989 | Haber et al. |
| 4,991,601 A | 2/1991 | Kasai et al. |
| 5,033,476 A | 7/1991 | Kasai |
| 5,048,537 A | 9/1991 | Messinger |
| 5,061,451 A | 10/1991 | Ganshirt et al. |
| 5,100,376 A | 3/1992 | Blake, III |
| 5,102,407 A * | 4/1992 | Carmen et al. ............. 604/410 |
| 5,114,400 A | 5/1992 | Lynn |
| 5,167,656 A * | 12/1992 | Lynn .......................... 604/409 |
| 5,270,003 A | 12/1993 | Bernes et al. |
| 5,372,143 A | 12/1994 | Bernes et al. |
| 5,395,347 A | 3/1995 | Blecher et al. |
| 5,464,397 A | 11/1995 | Powers, Jr. |
| 5,484,418 A | 1/1996 | Quiachon et al. |
| 5,496,301 A * | 3/1996 | Hlavinka et al. ........... 604/409 |
| 5,545,339 A | 8/1996 | Bormann et al. |
| 5,601,730 A * | 2/1997 | Page et al. .................. 210/188 |
| 5,620,008 A | 4/1997 | Shinar et al. |
| 5,665,074 A | 9/1997 | Kelly |
| 5,743,872 A | 4/1998 | Kelly |
| RE35,841 E | 7/1998 | Frank et al. |

FOREIGN PATENT DOCUMENTS

| | | |
|---|---|---|
| WO | WO 98/28057 | 12/1997 |
| WO | WO 00/24313 | 5/2000 |

OTHER PUBLICATIONS

International Search Report for PCT/US00/19076, dated Oct. 3, 2000.

* cited by examiner

*Primary Examiner*—Sharon Kennedy
*Assistant Examiner*—Catherine Serke
(74) *Attorney, Agent, or Firm*—Andrew G. Kolomayets; Michael C. Mayo; Denise M. Serewicz

(57) ABSTRACT

A blood sampling system for obtaining blood samples from a fluid flow path is disclosed. The sampling system includes a container that can be isolated from the remainder of a blood processing set and allows for collection of a sample either before or after the blood donation.

13 Claims, 11 Drawing Sheets

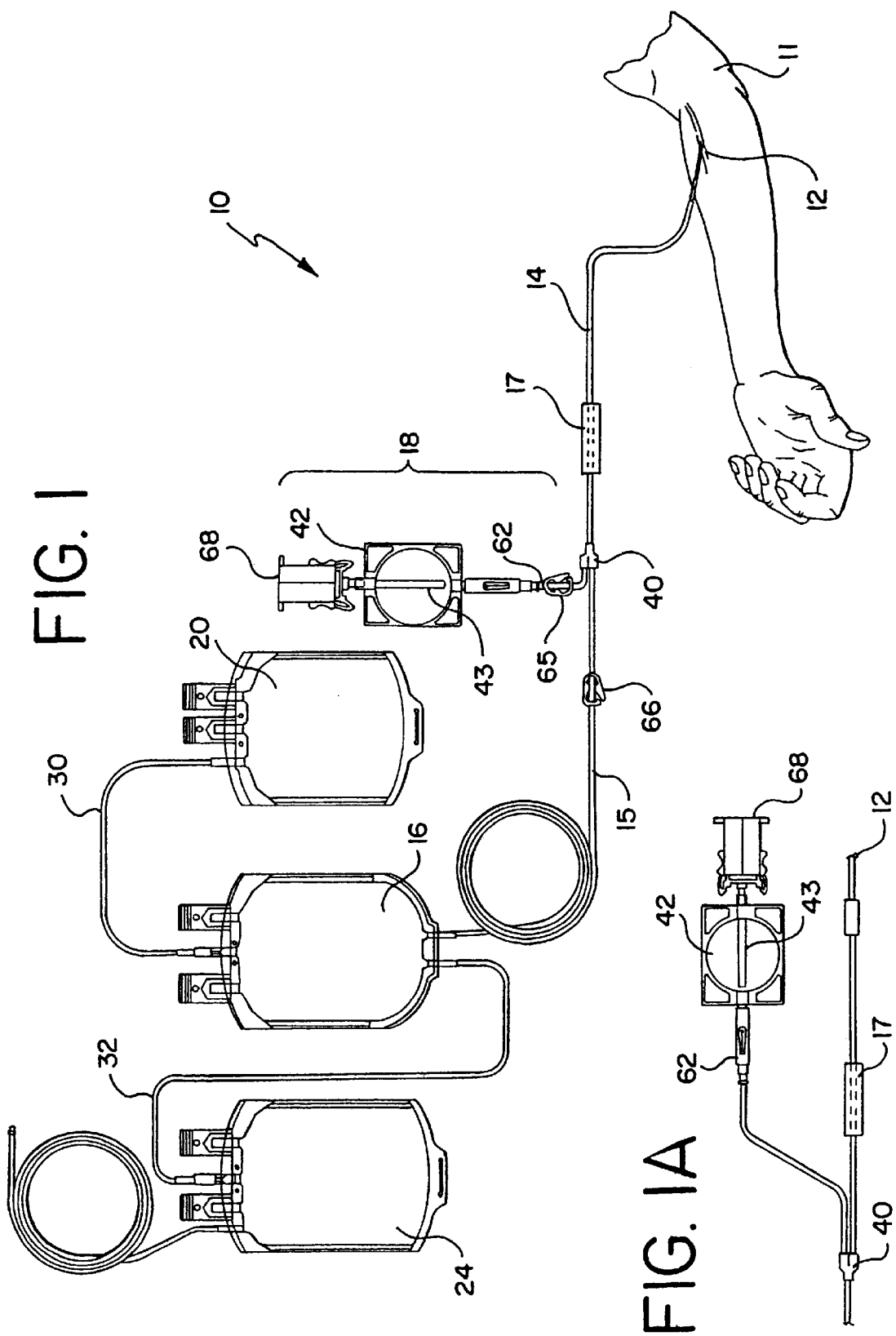

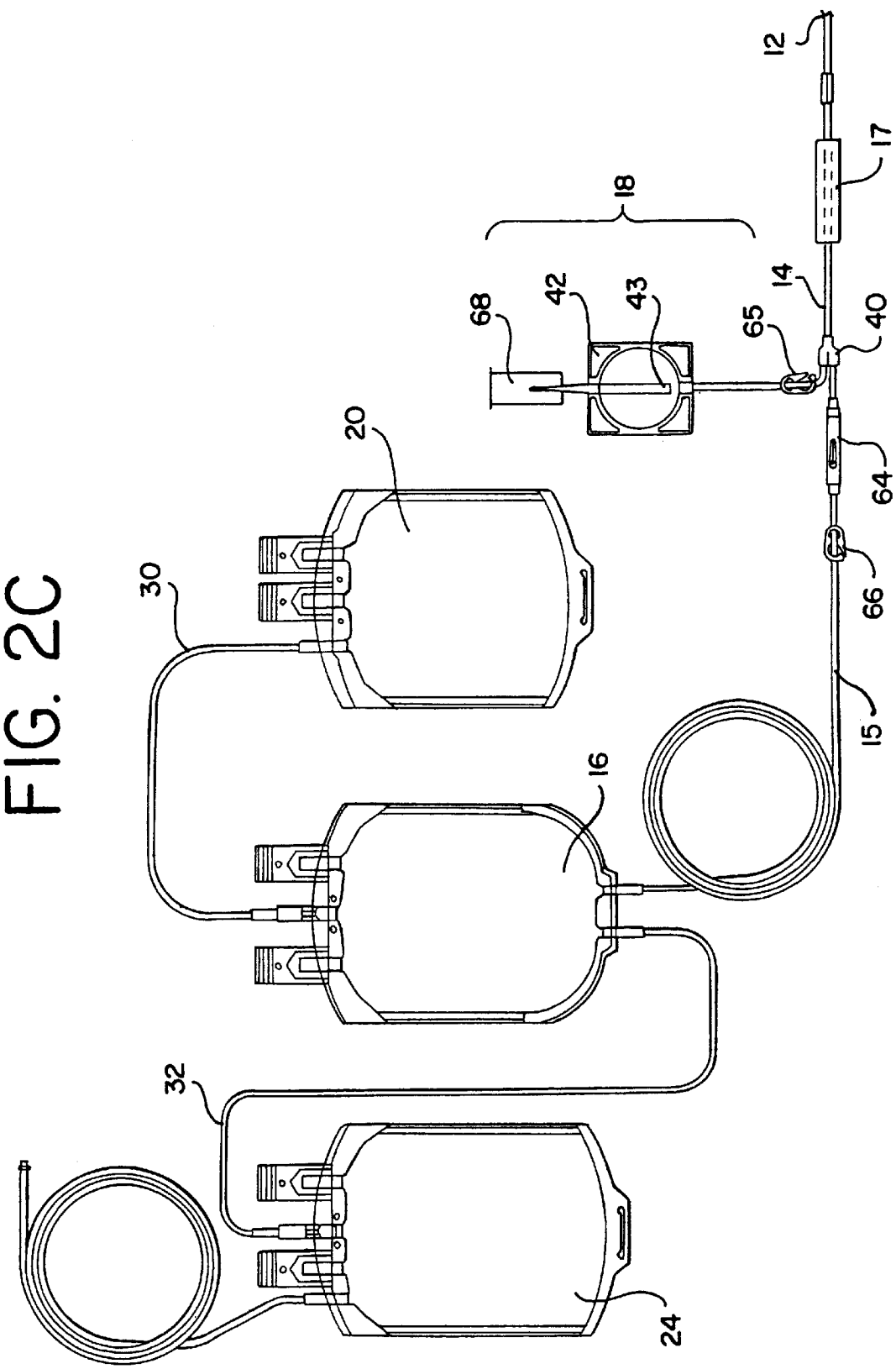

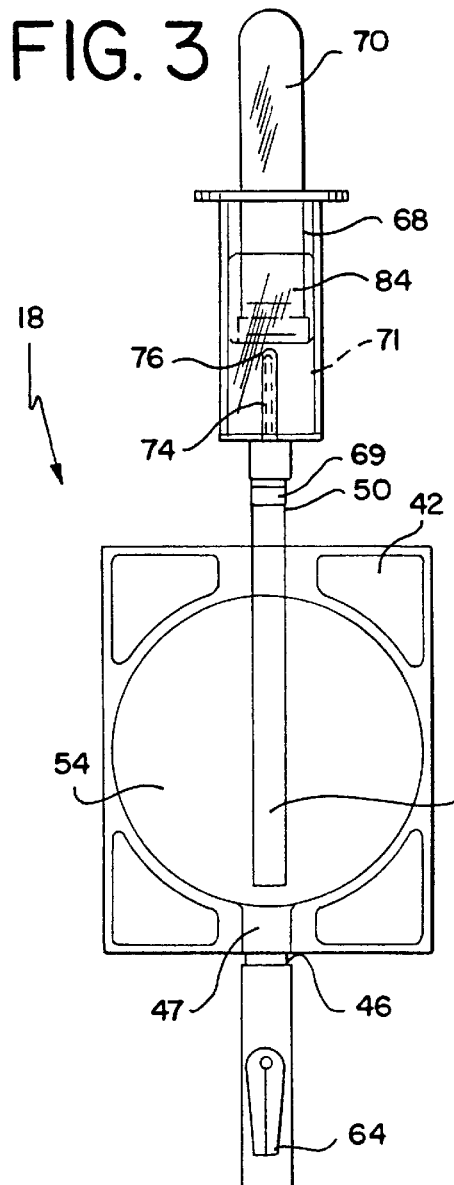
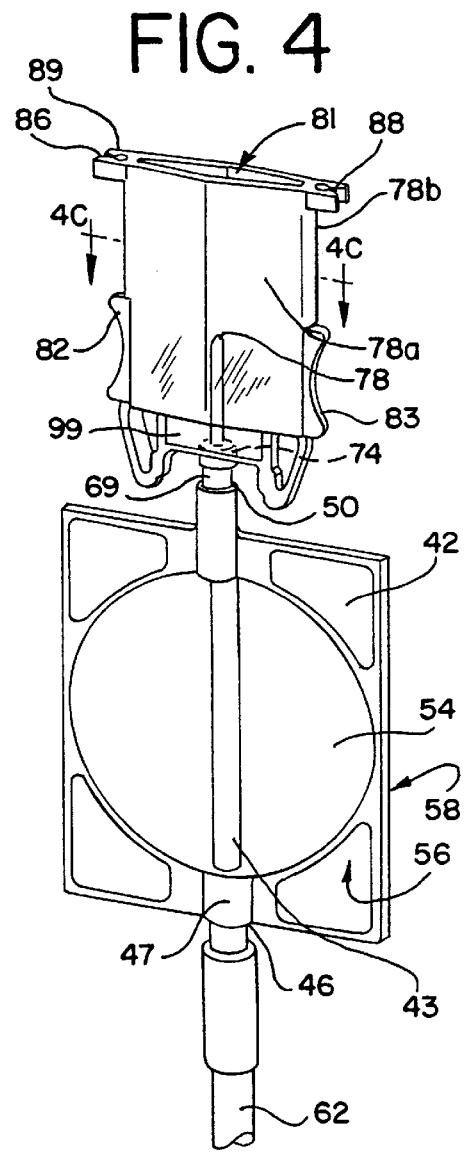
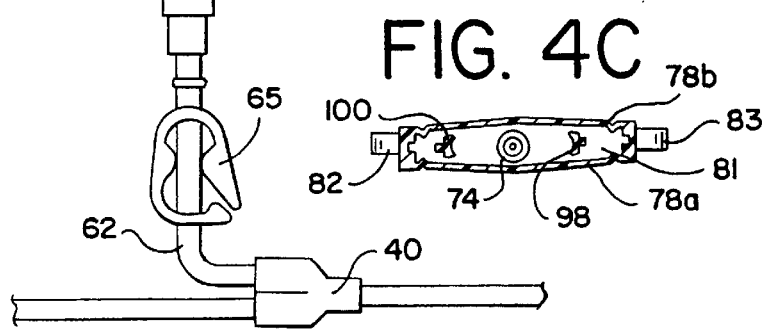

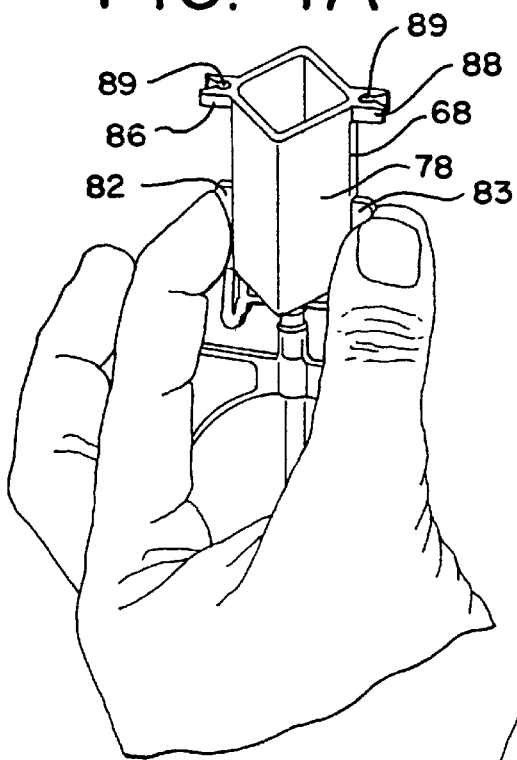
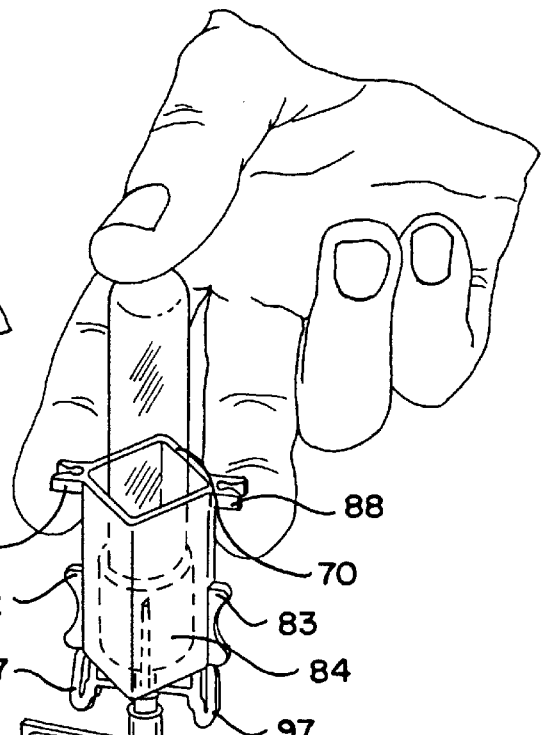
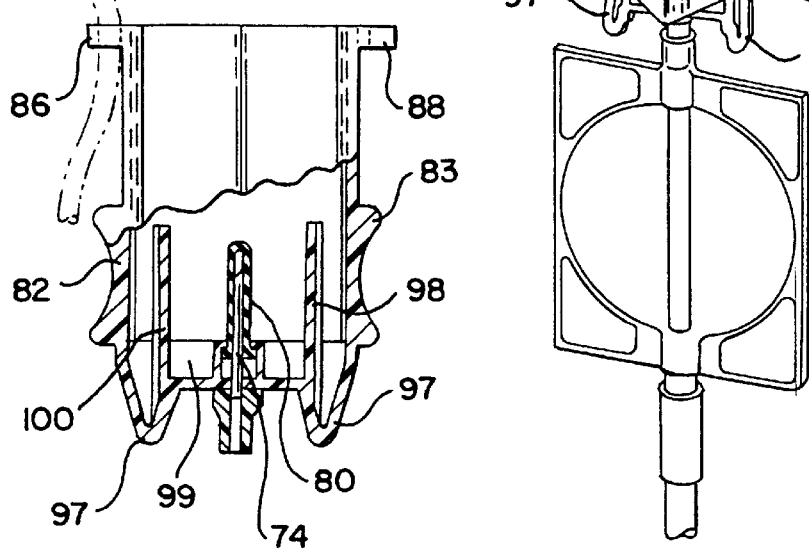

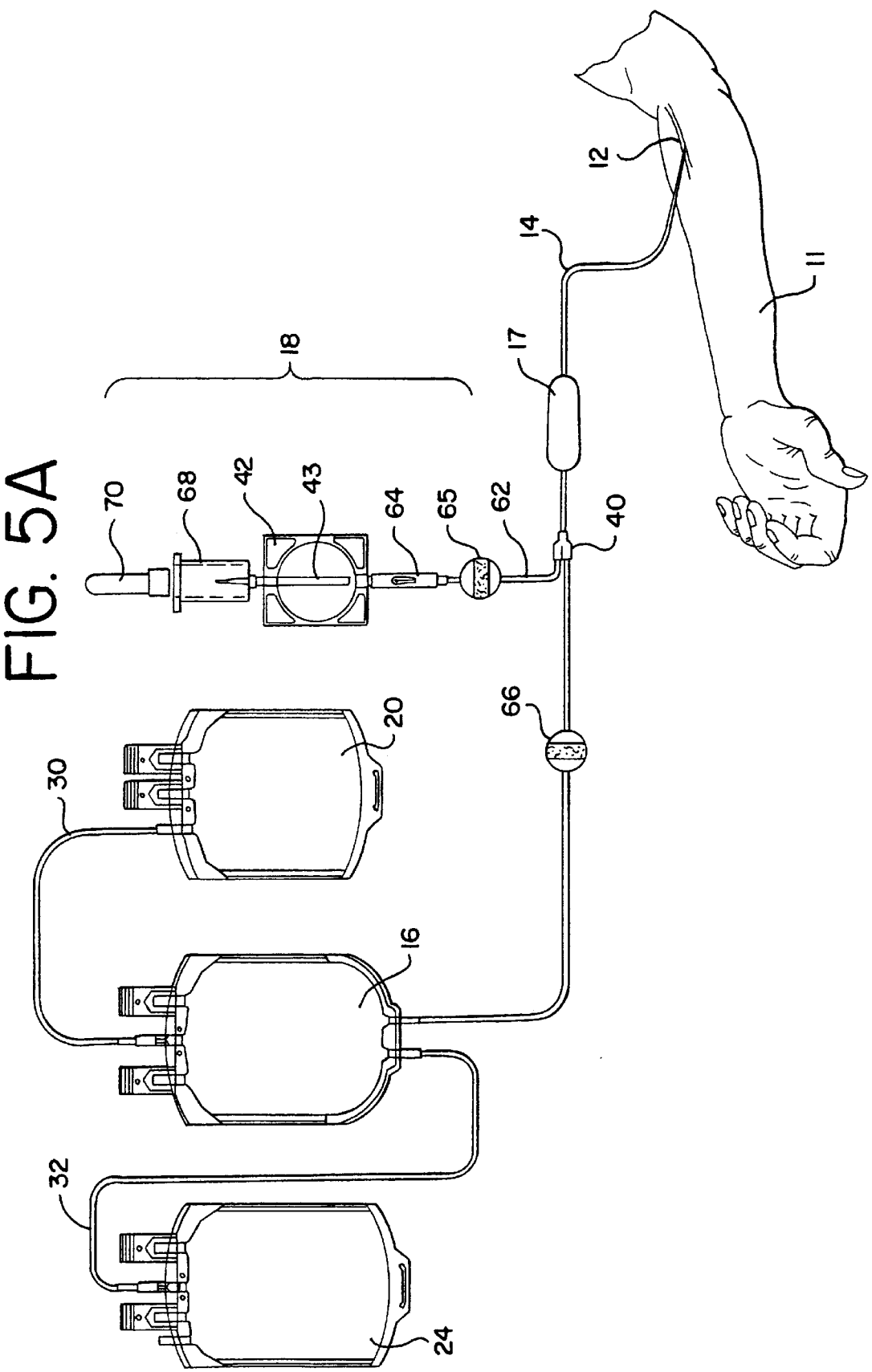

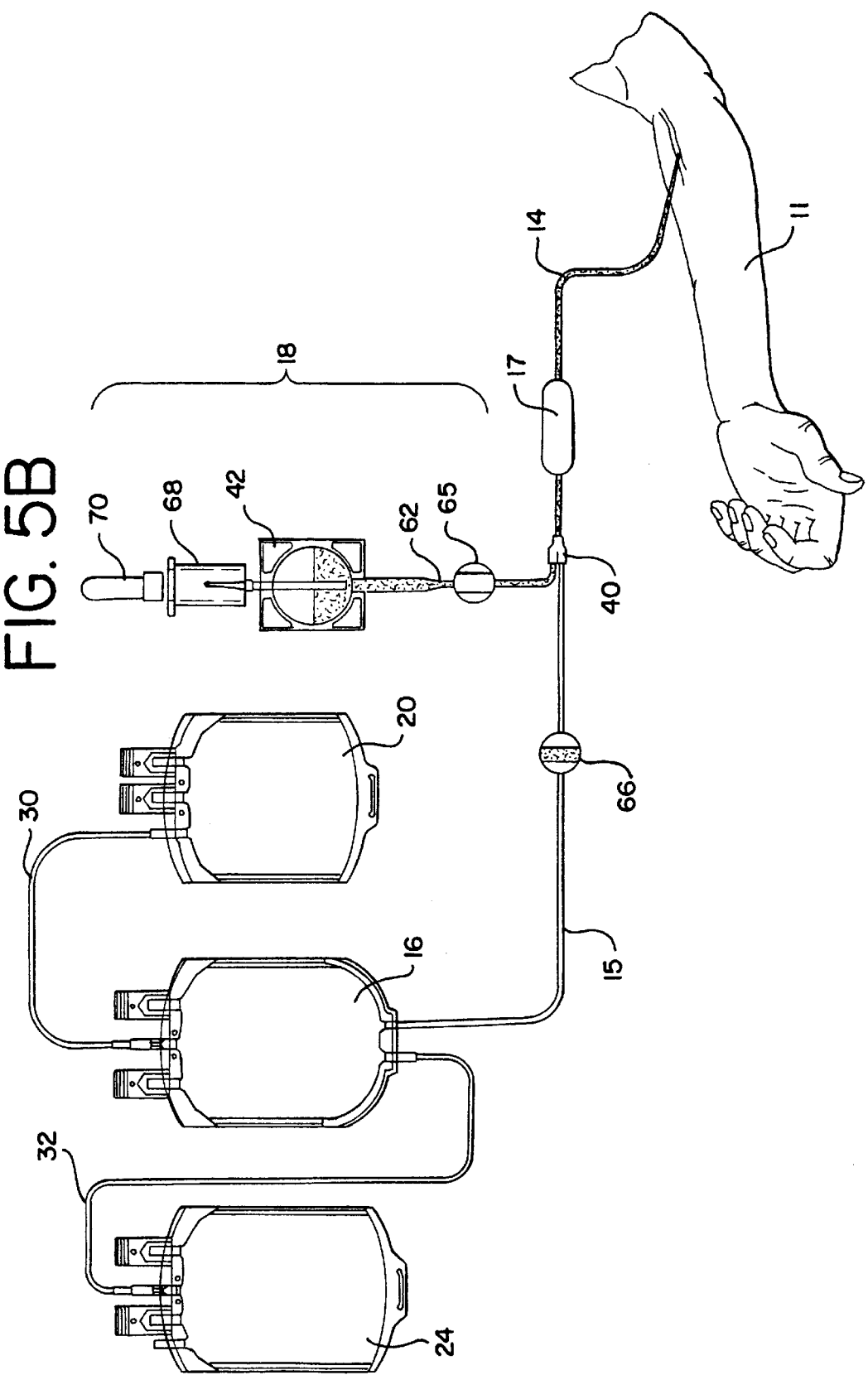

BLOOD PROCESSING SET INCLUDING AN INTEGRATED BLOOD SAMPLING SYSTEM

BACKGROUND OF THE INVENTION

The administration of blood or blood components often plays a critical role in the emergency and/or long term treatment of patients. Blood or the individual components of blood (such as platelets, plasma, red blood cells, etc.) may be administered or transfused to patients to treat a variety of conditions. For example, blood may be administered to a patient to replace blood lost as a result of trauma, while individual blood components may be administered as part of a longer term treatment of patients suffering from cancer or certain blood related diseases. The blood or blood components administered to the patient come from blood previously collected from donors.

One of the most common blood collection techniques, and perhaps the most well-known, is the "manual" collection of whole blood from healthy donors. As commonly understood and as used herein, "manual" collection refers to a collection method where whole blood is allowed to drain from the donor and into a collection container without the use of external pumps or similar devices. This is in contrast to the so-called "automated " procedures where blood is withdrawn from a donor and further processed by an instrument that typically includes a processing or separation device and pumps for moving blood or blood components into and out of the device.

Regardless of whether the blood collection technique is manual or automated, withdrawing blood from the donor typically includes inserting a vein access device, such as a needle, into the donor's arm (and, more specifically, the donor's vein) and withdrawing blood from the donor through the needle. The "venipuncture " needle typically has attached to it, one end of a plastic tube that provides a flow path for the blood. The other end of the plastic tube terminates in one or more preattached plastic blood containers or bags for collecting the blood. The needle, tubing and containers make up a blood processing set which is presterilized and disposed of after a single use.

In the manual technique, the collection container and plastic tubing may also include a volume of a liquid anticoagulant, while in the automated technique, a separate container of anticoagulant may be provided from which the anticoagulant is metered into the flow path and mixed with the incoming whole blood. In any event, anticoagulant is required because of the tendency of blood to clot and adhere to the walls of the plastic surfaces which it contacts.

An important consideration in any blood collection technique or system is ensuring that the system or set does not become contaminated by airborne bacteria or other foreign substances that may compromise the sterility of the system. Thus, the sterility of the above-described disposable blood processing set or system is maintained by minimizing exposure of the flow paths and interiors of the blood containers to the outside environment. Such systems are commonly referred to as "closed " systems.

After collection but prior to transfusion to a patient, the blood is typically tested for determining blood type and the presence of pathogens such as virus, bacteria and/or other foreign substances in the donor's blood. Typically, testing of the collected blood requires obtaining a sample of the blood from the blood donor at or near the time of collection.

One well-known technique of obtaining a blood sample is to simply withdraw or collect the blood remaining in the flow path of the disposable set after donation. This involves removing the needle from the donor, inserting the needle into a vacuum sealed sampling vial or tube and allowing the blood from the flow path to drain into the vial. However, because there is a limited supply of blood remaining in the flow path, there may not be enough blood to provide enough of a sample to perform all of the required or desired testing. Accordingly, if a larger volume or numerous samples of blood are required, the technician obtaining the sample may continue draining the blood from the tubing, eventually withdrawing the collected anticoagulated blood from the collection container. Withdrawing blood from the collection container, however, may be less desirable in that it may expose the collected blood in the collection container to the outside environment. Withdrawing blood from the collection container for sampling also reduces the volume of available blood for later processing and transfusion.

An alternative to collecting anticoagulated blood from the collection container is to clamp off the flow path near the collection container and divert the blood being withdrawn from the donor to a collection (sampling) vial or tube of the type described above. This procedure typically employs a particular type of disposable tubing set having a preattached sampling site on the main flow path. Blood at or near the sampling site may be obtained by piercing the sampling site with a separately provided needle or other piercing device, and attaching a sampling vial thereto. To minimize the risk that the incoming blood (which is intended for later processing and transfusion) will be exposed to the outside environment, the sample is typically collected after completion of the blood donation.

Still another example of a blood sampling system is described in U.S. Pat. No. 5,167,656, which is assigned to the assignee of the present application. That patent describes a disposable tubing set wherein the flow path includes an enlarged sample collection portion. Blood for sampling is collected in the enlarged portion by clamping off the flow path near the collection container and allowing the enlarged tubing portion to fill with blood. Once the desired volume of blood for sampling is collected in the enlarged tubing portion, the needle is removed from the donor and the blood is transferred to a vial by piercing the cap of the vial with the needle and allowing the blood to drain into the sampling vial.

While these known techniques have generally worked satisfactorily, efforts continue to provide further improvements in the area of blood sampling. For example, as set forth above, the sample is typically obtained after the blood product (intended for further processing and transfusion) has been collected so as to preserve the sterility of the closed system. However, if the donation procedure must be terminated before completion, there may not be an opportunity to obtain a sample directly from the donor. Thus, it would be desirable to provide a sampling system in which blood samples can be obtained either before or after donation, but without the risk of compromising the sterility of the system and/or the collected blood product.

In addition, as discussed above, the use of vacuum-filled tubes or vials is common in blood sampling processes. When such vacuum-filled tubes are used, there is the possibility that the suction may cause the tubing of the blood processing set to collapse and restrict blood flow. Of even greater concern, particularly in small-veined donors, is the possibility that the suction may cause the donor's vein to collapse. Thus, it would also be desirable to provide a sampling system where the risk of donor vein or tubing collapse is minimized.

Finally, it would also be desirable to provide a sampling system which is integrated with the blood collection set and requires few separate or external components.

SUMMARY OF THE INVENTION

The foregoing benefits are achieved by the present invention which, in general, is directed to a device, system and method for obtaining liquid samples from a blood donor.

In one aspect, the present invention is embodied in a container for receiving a biological fluid, such as blood. The container includes a pair of oppositely facing walls joined together to define a generally circular interior chamber. The container further includes an inlet port and an outlet port. A tubing segment defining a fluid flow path communicates with the outlet port and extends substantially into the interior chamber of the container.

In another aspect, the present invention is embodied in a disposable processing set. The disposable blood processing set includes a first container that is adapted for receiving blood from a donor and a vein access device. The disposable processing set includes a first tubing segment that defines a first flow path between the container and the vein access device. A second container for receiving blood from a donor is also included. The second container includes an inlet port, an outlet port and a tubing communicating with the outlet port and extending substantially into the interior chamber of the second container. The second tubing segment defines an openable flow path between the second container and the vein access device.

In another aspect, the present invention is embodied in a method for obtaining a blood sample from a donor. The method includes providing a blood processing set that has at least a blood collection container and a sampling container. The processing set also includes a vein access device and first and second tubing segments for establishing flow communication between the containers and the vein access device. The method further includes withdrawing blood from a donor through the vein access device and introducing the blood into the sampling container at one end of the sampling container. After introduction of the blood into the sampling container, the flow path between the sampling container and the donor is isolated. The blood is withdrawn from the sampling container at an end that is opposite to the first end of the sampling container. Blood from the donor may be introduced into the collection container after isolation.

In another aspect, the present invention is embodied in a holder for receiving a blood sampling tube or vial. The holder includes a first end, a second end and a central body portion between the ends. The body portion may include two opposed flexible walls defining an interior pocket. A piercing member is disposed inside the pocket. The body portion may be flexed from a closed position to an open position for receiving a sampling vial.

BRIEF DESCRIPTION OF THE DRAWINGS

FIG. 1 is a perspective view of a disposable blood collection or processing set including a sampling system embodying the present invention;

FIG. 1A is a perspective view of a portion of an alternative disposable blood collection or processing set including a sampling system embodying the present invention;

FIG. 2C is a perspective view of another variant of a disposable blood collection or processing set including a sampling system embodying the present invention;

FIG. 3 is a perspective view of the sampling system embodying the present invention;

FIG. 4 is a perspective view of the sampling system of FIG. 3 with an another embodiment of the holder;

FIG. 4A is a perspective view of the sampling system of FIG. 4 with the holder open;

FIG. 4B is a perspective view of the sampling system of FIG. 4 with the sampling vial disposed within the holder;

FIG. 4C is a cross-sectional view of the holder of FIG. 4, taken along 4C—4C.

FIG. 4D is a partial cross-sectional view of the holder of FIG. 4 with a portion broken away to show the interior of the holder;

FIG. 5A is a diagram showing one step in the method of obtaining a blood sample in accordance with the present invention;

FIG. 5B is a diagram showing the step of collecting a blood sample in accordance with the present invention;

DETAILED DESCRIPTION OF THE DRAWINGS

Figure 2A:
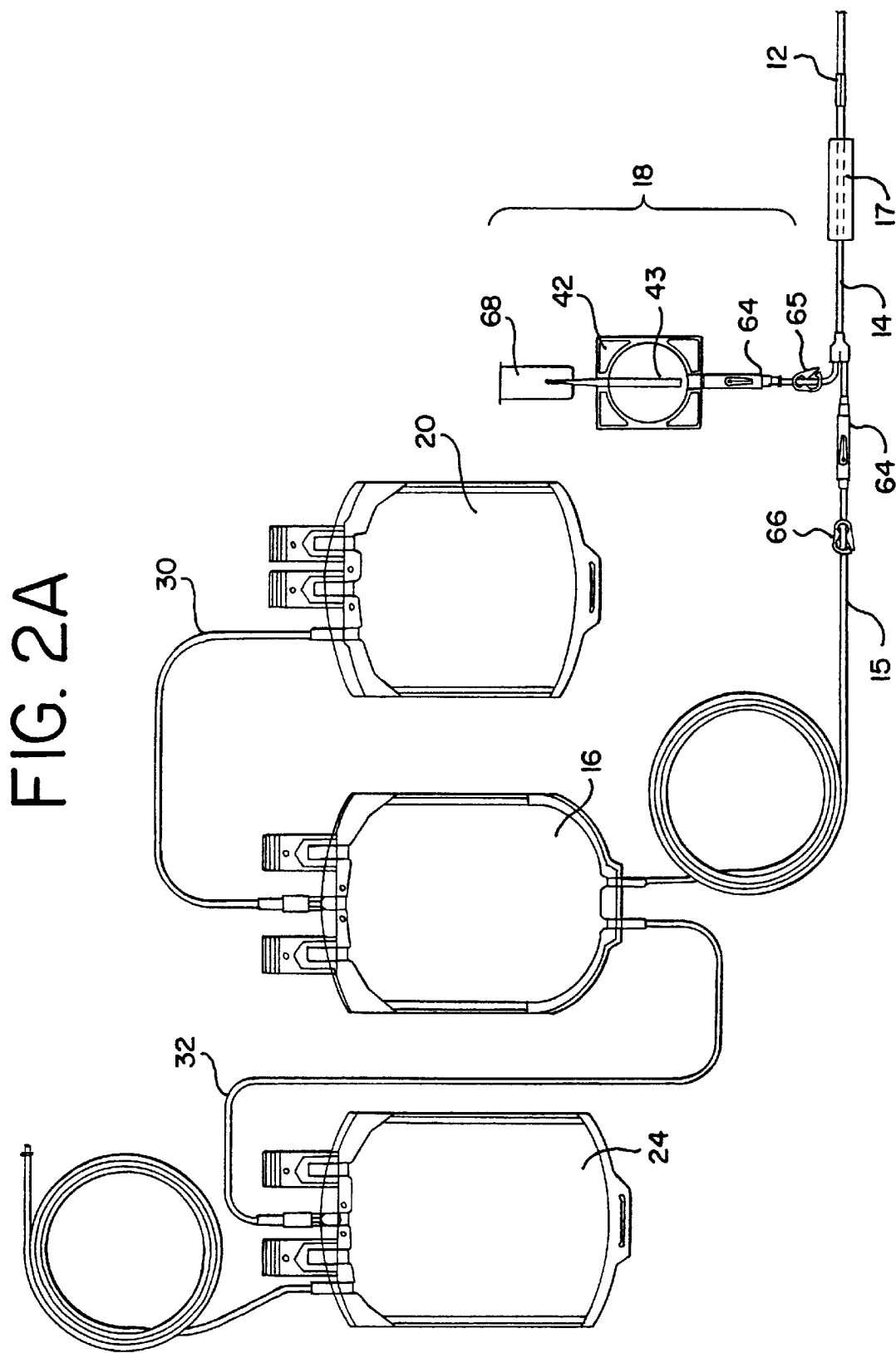
FIG. 2A is a perspective view of another variant of a disposable blood collection or processing set including a sampling system embodying the present invention.

Turning now to FIG. 1 of the drawings, the present invention may be embodied in a liquid flow conduit set such as a disposable processing set 10, which is particularly suitable for use in the manual collection of blood from a donor 11. The illustrated disposable set 10 may include a needle such as venipuncture needle 12, and plastic tubings 14 and 15 extending from needle 12 to a collection container such as a flexible plastic container 16. A needle protector 17 may also be provided for retraction and storage of needle 12 after use.

The blood processing set 10 may include a single blood collection container 16 or, more preferably, as shown in FIG. 1, may be a multiple blood container system including additional containers 20 and 24. In accordance with the present invention, disposable processing set 10 includes a sampling system 18, described in more detail below.

As set forth above, blood processing set 10 may include a primary container 16 and one or more integrally attached transfer containers 20 and 24. During use, primary container 16 (sometimes referred to as the donor bag) receives whole blood from the donor through integrally attached donor tubings 14 and 15 and venipuncture needle 12. Container 16 typically includes a suitable anticoagulant such as citrate phosphate dextrose (CPD), citrate phosphate dextrose adenine (CPDA) or acid citrate dextrose (ACD).

Containers 20 and 24 may be attached to primary container 16 by integrally attached transfer tubing 30 and 32. Containers 20 and 24 are provided to receive blood components such as, but not limited to, red blood cells and plasma that have been separated from whole blood. For example, collected whole blood in container 16 may be centrifuged to separate the blood into layers of such components. The heavier cellular components, such as red blood cells, settle to the bottom of the container 16 and the lighter, less dense components, such as plasma (with or without platelets), remain in the top layer. The components may then be separated by expressing the lighter components through transfer tubing and into container 20. Likewise, the heavier components may be expressed through transfer tubing 32 to container 24. Such "top and bottom" separation techniques and disposable processing sets are well known and are available from Baxter Healthcare Corporation of Deerfield, Ill. under the name Optipaco®.

Of course, it will be understood that the present invention is not limited to the processing sets shown in the figures and that processing sets having different container and tubing configurations are also within the scope of the present invention. For example, a multiple container system wherein tubing segments 30 and 32 are both attached to container 16 at or near the top of container 16 may also be used. Container 24 may include a volume of a preservative or storage solution which is introduced into container 16 and combined with separated red cells after plasma has been expressed to container 20. Such blood processing sets are also available from Baxter Healthcare Corporation.

Containers 16, 20 and 24 and associated tubing segments of processing set 10 are typically made from conventional and approved medical grade plastic materials. One such material may be polyvinyl chloride that includes a plasticizer such as, but not limited to, plasticizers selected from the family of citrate esters, which are described in U.S. Pat. Nos. 5,167,657, 5,100,401 and 5,026,347, all of which are incorporated by reference herein. Containers made from polyvinyl chloride plasticized with citrate ester or other plasticizers are available from Baxter Healthcare Corporation of Deerfield, Ill. Alternatively, and depending in part on the blood components to be stored, containers may be made from other materials such as polyolefin materials with or without plasticizer.

Turning now to the sampling system, as shown in FIG. 1, sampling system 18 may be integrally attached to the disposable processing set 10 at Y-connector 40. In general, and as shown in greater detail in FIG. 3, sampling system 18 may include a container 42 having an inlet port 46 and outlet port 50. Container 42 further includes an interior chamber 54 defined by walls 56 and 58 (FIG. 4) that are joined together in a facing arrangement. Walls 56 and 58 may be made from sheets of extruded plastic. Container 42 may be made by heat sealing together walls 56 and 58 or by any other method known to those of skill in the art. Preferably, walls 56 and 58 may joined together by radio frequency (RF) sealing the walls substantially along their peripheries. A bushing 47, (typically made of polyvinyl chloride) may be included at, for example, inlet port 46, and may also be RF sealed to walls 56 and 58.

Container 42 (or the walls 56 and 58) may typically be made of any conventional medical grade plastic material that is sterilizable by known sterilization techniques including autoclaving. One such preferred material is polyvinyl chloride with a plasticizer, such as a citrate ester (e.g. n-butyryltri-n-hexyl citrate), as substantially described above. Of course, other known plasticizers such as TEHTM and DEHP may also be used. In one example, the material used to make walls 56 and 58 may include approximately 70%, by weight, polyvinyl chloride and approximately 30%, by weight, plasticizer.

Container 42 may also include drain tube 43. As shown in FIGS. 3–4, one end of drain tube 43 is attached to container 42 and may provide outlet port 50. Preferably, drain tube 43 may be RF sealed to container walls 56 and 58. Drain tube may be made of any typical medical grade material such as polyvinyl chloride with a plasticizer. Drain tube 43 extends substantially into interior chamber 54 and terminates near inlet port 46. Extending drain tube 43 substantially into interior chamber 54 assures that the end of drain tube 43 will reside within or near the liquid inside container 42, making it less likely that air will be present when liquid (such as blood) is withdrawn from container 42 into a sampling vial. Tube 43 also separates walls 56 and 58 to provide chamber 54 and assists in preventing walls 56 and 58 from collapsing during, for example, heat sterilization. As shown in FIG. 3, in a preferred embodiment, interior chamber 54 may be generally circular. This may allow, for more complete drainage of container 42 by eliminating corners where the blood may be retained. In one embodiment, interior chamber of container 42 may have a volume of approximately 20–50 ml and, more preferably, approximately 30–40 ml.

As further shown in FIG. 3, sampling device 18 may include tubing segment 62 attached to container 42 at inlet port 46. Tubing segment 62 may be attached to container 42 and, more specifically, bushing 47 by, for example, solvent bonding. The other end of tubing segment may be bonded to Y-connector 40. Tubing segments 62 may further include an openable barrier 64 such as a frangible cannula or connector of the type described in U.S. Pat. No. 5,330,464, assigned to the assignee of the present application and incorporated by reference herein. Barrier 64 preserves the sterility of the flow path defined by tubing segment 62. Flow restrictor clamps, such as Roberts clamps 65 and 66 (FIG. 1), on tubing segment 62 and tubing segment 15 may also be provided to allow for flow control through blood processing set 10 by the technician.

Sampling device 18 may further include a receptacle or holder 68 as shown in FIG. 3. As will be described in more detail below, holder 68 is adapted to receive a blood sampling vial 70. Holder 68 may be attached to container 42 at outlet port 50 to provide an integrated system. In one embodiment, holder 68 includes distal end port 69 which may be mated with and bonded to outlet port 50 prior to heat sterilization. More preferably, distal end port 69 may be bonded to drain tube 43. Subsequent heat sterilization forms a bond between the polycarbonate material of distal end port 69 and, for example, drain tube 43. Of course, other ways of bonding holder 68 to container 42, such as solvent bonding, may also be used. Alternatively, holder 68 may be separately provided and attached to outlet port 50 at the time of use.

In one embodiment (shown in FIG. 3), holder 68 may have a central body portion 71, generally in the shape of a hollow cylinder. Holder 68 is open at its proximal end to allow for insertion of sampling vial 70. Holder 68 may be made of any plastic sterilizable material. Holders of the type generally discussed above are available from, for example, Becton-Dickinson Co. of Franklin Lakes, N.J.

Holder 68 may include a piercing member 74 as generally shown in FIG. 3 (or FIGS. 4 and 4C). Piercing member 74 may be a needle, cannula or other biocompatible device having a sharpened tip. As set forth above, piercing member 74 includes a piercing end 76. Piercing member 74 may be made of any material of sufficient strength such as metal or plastic. In addition, end 76 of piercing member 74 may be enclosed within a protective sheath 80 (best shown, for example, in FIG. 4C). Protective sheath 80 may preferably be made of a flexible material, such as latex, which is capable of being penetrated by the tip of piercing member end 76. Also protective sheath 80 should be sufficiently resilient to return to its original shape (covering end 76) upon withdrawal of sampling vial 70.

In an alternative embodiment, holder 68 may be provided in the form of a flexible pocket, as generally shown in FIG.

4. As shown in FIG. 4, holder 68 may include a generally rectangular body portion having oppositely facing walls 78a and 78b, which define an interior pocket 81. Walls 78a and 78b are longitudinally hinged or creased to allow for flexing of holder 68 as shown in FIG. 4A. In a preferred embodiment, walls 78a and 78b may include pinching tabs 82 and 83 for compression by the technician to flex open interior pocket 81 as generally shown in FIG. 4A. Springs 97 are compressed when pinching tabs are squeezed, but return to their normal expanded position when pressure on the tabs 86 and 88 is withdrawn, thereby returning holder 68 to its "closed" position (which protects the user from the possibility of an accidental needle stick).

Holder 68 shown in FIGS. 4–4C may further include finger grasping tabs 86 and 88. Finger grasping tabs 86 and 88 provide grasping areas for the operator when inserting sample vial 70 a shown in FIG. 4B. As shown in FIG. 4B, finger grasping tabs 86 and 88 may further include apertures 89 for retaining tubing segments before, during and after use of disposable processing set 10. In addition, holder 68 shown in FIGS. 4–4D may further include positioning prongs 98 and 100. Positioning prongs 98 and 100 are laterally spaced relative to piercing member 74 and assist in guiding vial 70 over piercing member 74. Holder 68 shown in FIG. 4–4D may further include a reservoir 99 to retain any uncollected drops of blood. Holder 68 of FIG. 4 may typically be made of any suitable sterilizable and flexible material such as polyolefin and, preferably, polyethylene, by casting, injection molding or other techniques known to those of skill in the art. As in the embodiment of FIG. 3, the holder shown in FIGS. 4–4D may also include a distal end port 69 made, for example, of polycarbonate or other suitable material, that may be bonded to outlet port 50 and/or drain tube 43 during heat sterilization. Of course, other ways of bonding holder 68 to container 42 may also be used.

During a collection procedure, a sampling vial 70, as shown in FIG. 3, may be inserted into the interior of holder 68. As shown in FIGS. 3 and 4B, vial 70, which is typically a vacuum sealed vial, may itself include a piercable cap 84. Such vials are available from the Becton-Dickinson Co. of Franklin Lakes, N.J. and are sold under the trade name VACUTAINER®.

The method of collecting a blood sample from a donor during a blood donation using the blood processing system generally described above will now be described. In one embodiment, at the outset of the donation procedure, disposable processing set 10 may be provided with clamps 65 and 66 in a closed position, as shown in FIG. 5A. Next, frangible connector 64 is opened and needle 12 is inserted into the arm of the donor 11. As shown in FIG. 5B, clamp 65 is opened and container 42 is allowed to fill with the blood from the donor. Alternatively, clamp 65 may be opened prior to venipuncture.

Figure 5C:
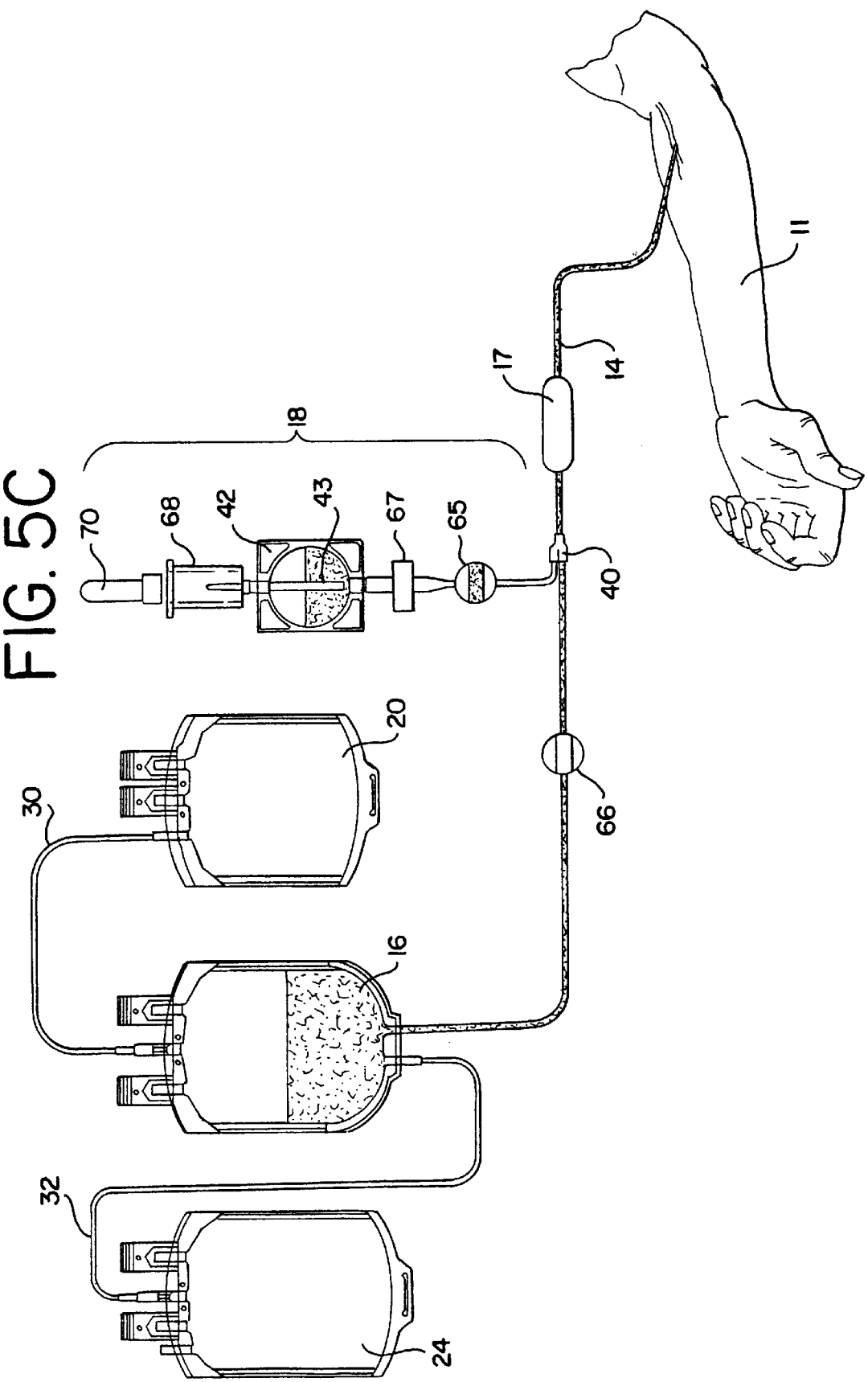
FIG. 5C is a diagram showing the steps of isolating the blood sampling system from the remainder of the processing set and collecting blood in the collection container.

Once a sufficient volume of blood for sampling has been collected, sampling system 18 may be isolated from the remainder of the processing set 10 by heat sealing tubing segment 62 in ways that are known to those of skill in the art. One device that may be used for sealing is the tubing sealing device known as the Hematron®, sold by Baxter Healthcare Corporation. Alternatively, line 62 may be sealed by a metal retaining clip or other means known to those of skill in the art. After isolation by seal 67, clamp 65 is closed and the clamp 66 is opened to allow blood flow into container 16 as shown in FIG. 5C.

Figure 5D:
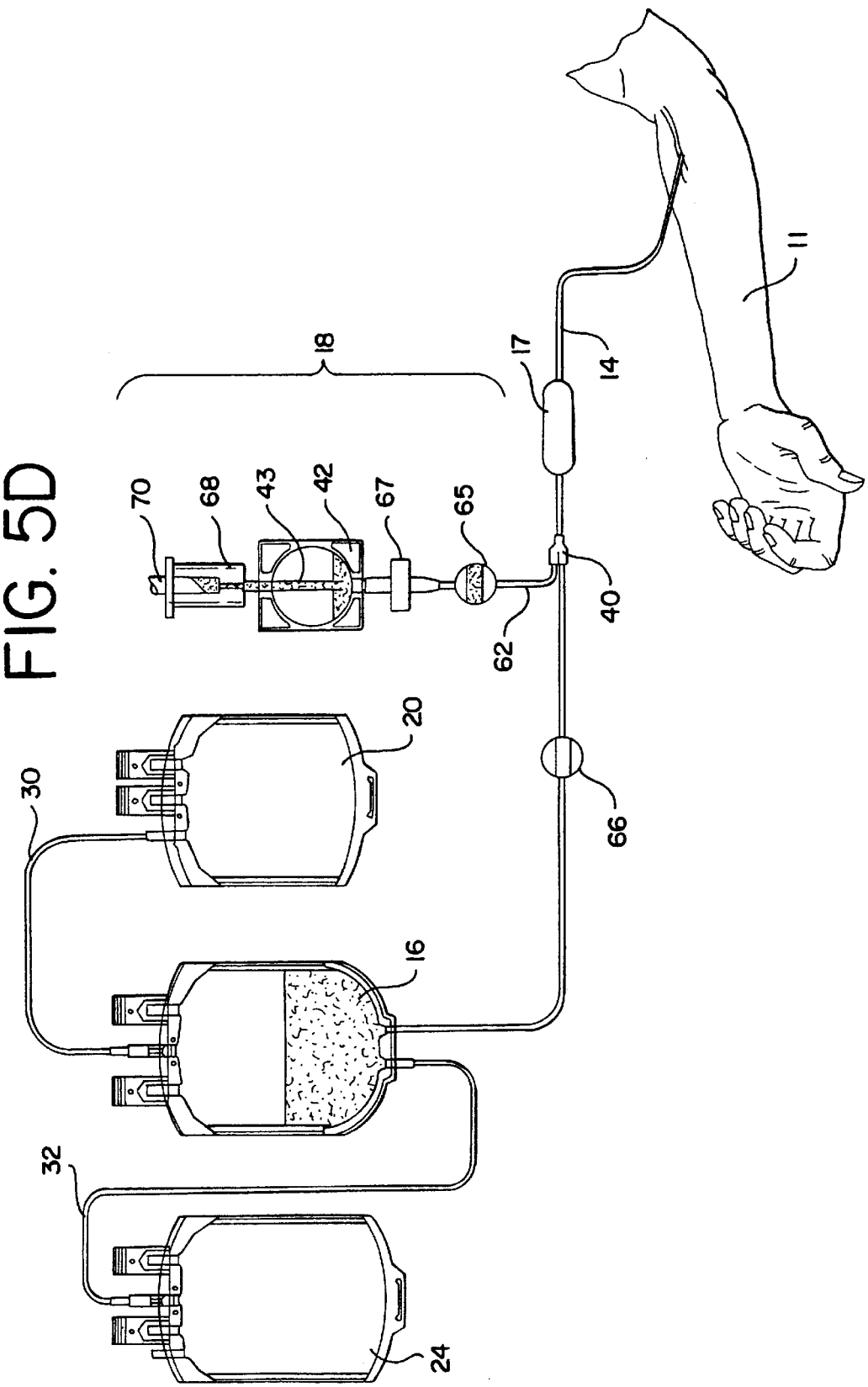
FIG. 5D is a diagram showing the step of withdrawing the blood sample from the sampling container and collecting it in a sampling vial.

Once sampling system 18 has been isolated from the remainder of the blood processing set 10, blood collected in container 42 may be transferred to a sampling vial 70 as shown in FIG. 5D and in more detail in FIGS. 3 and 4C. Sampling vial 70 is inserted into the interior of holder 68 so that cap 84 of vial 70 is pierced by the piercing end 76 of piercing member 74, as generally shown in FIG. 4B. As shown in FIGS. 3 and 4, it is preferred that sampling vial 70 be introduced into holder 68 in an inverted position so that blood flows up into vial 70. Applicants have discovered that such blood flow results in less hemolysis of red blood cells as compared to other collection techniques where the blood is allowed to drip into an upright vial.

Finally, turning briefly to FIGS. 1A and 2A–2D, the blood processing sets shown therein are variants of the processing set 10 of FIG. 1. While the sampling system 18 shown in these embodiments is similar to the sampling system described above, the processing sets differ, in general, in the location of openable barriers 64, the orientation of certain components and the like. For example, the blood processing set shown in FIG. 1A is virtually identical to the set of FIG. 1 with the exception that Y-connector 40 is oriented in the opposite direction (which may be desirable for packaging purposes).

Figure 2B:
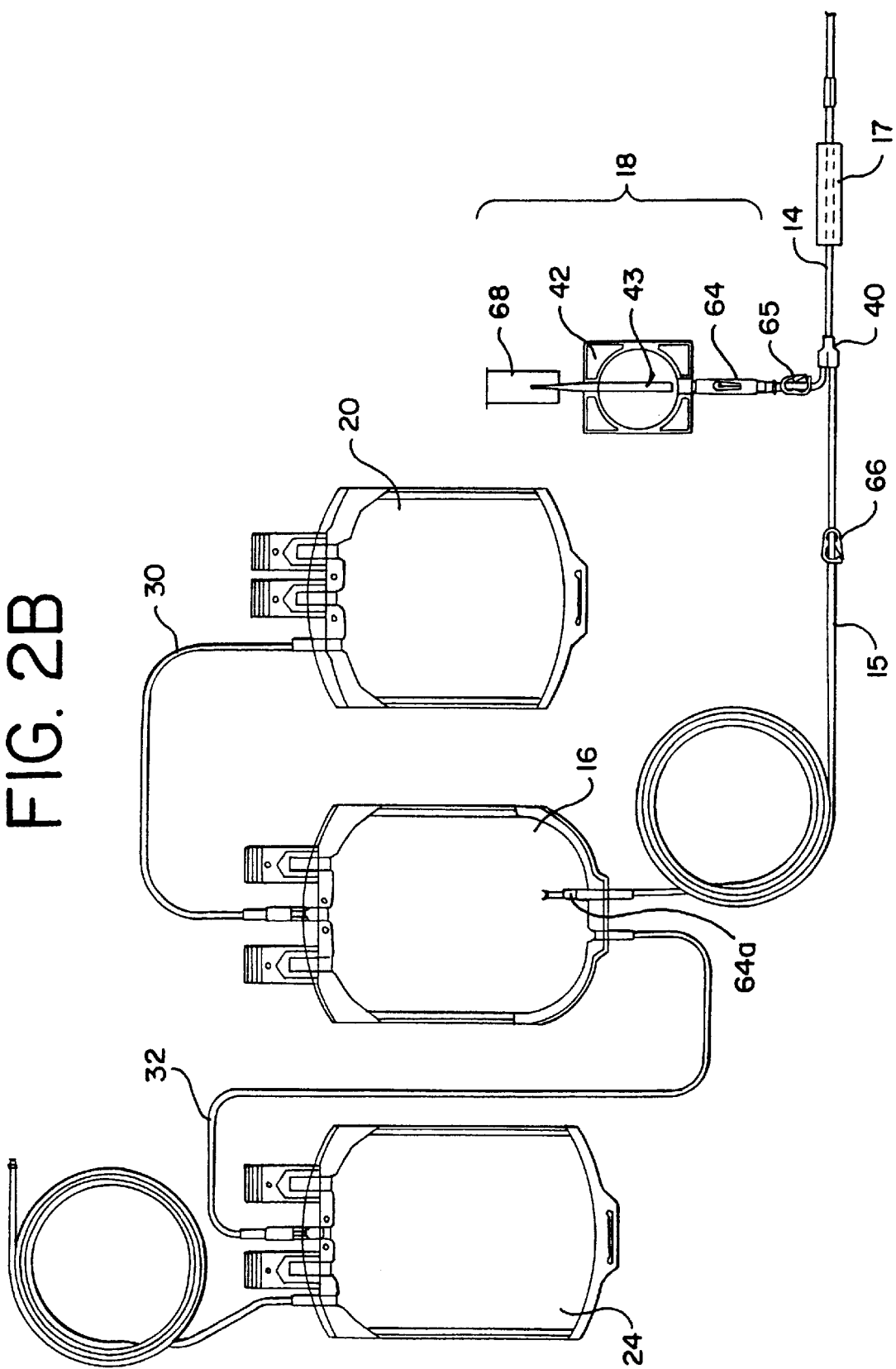
FIG. 2B is a perspective view of another variant of a disposable blood collection or processing set including sampling system embodying the present invention.

In FIG. 2A, an additional openable barrier 64 of the type described above may be included on line 15. Inclusion of barrier 64 on line 14 may prevent additional anticoagulant from entering line 14 distal to Y-connector 40. A similar but alternative embodiment is shown in FIG. 2B where an openable barrier 64a (such as a polyvinyl chloride frangible cannula) is located near the inlet port of container 16. In these embodiments, barrier 64 or 64A would be opened just prior to collection of blood in container 16.

Figure 2D:
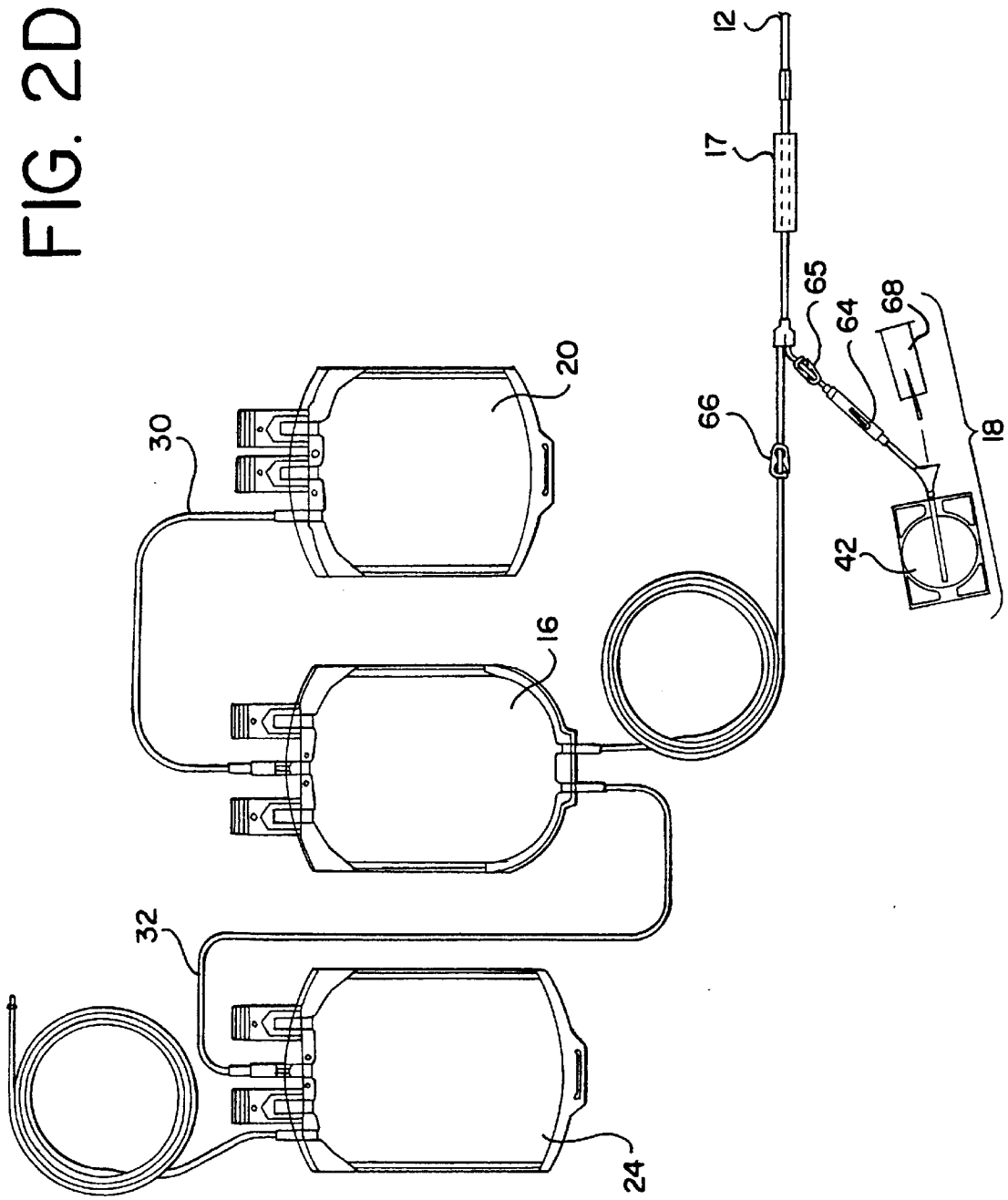
FIG. 2D is a perspective view of another variant of a disposable blood collection or processing set including a sampling system embodying the present invention.

In another embodiment, shown in FIG. 2C, an openable barrier 64 may be included on line 14, but not on line 62. In this embodiment, holder 68 preserves the sterility of the system. Finally, as shown in FIG. 2D, a Y-connector of the type described in U.S. Pat. No. 5,372,143, which is incorporated by reference herein, may be used in combination with the sampling system 18 of the present invention.

The disposable processing set and sampling system of the present invention provide many benefits. One benefit is that a blood sample may be obtained prior to the donation while still preserving the sterility of flow path between the donor and collection container. Specifically, as described above, a blood sample may be collected in container 42, which container may then be isolated from the remainder of the system (by, for example, sealing or clipping). Once container 42 has been isolated, a sampling vial may be introduced into the holder of the sampling system without the risk that bacteria or other foreign substances on the vial will contaminate the rest of the blood processing set, including flow path 14.

An advantage of pre-donation sampling is that bacteria or foreign substances that may be present on the donor's skin will not be transmitted to collection container 16, but will be diverted to sampling container 42.

Another advantage of pre-donation sampling is that it allows for collection of sample for testing, even if the donation is not completed.

Another advantage of pre-donation sampling is that it may provide a more accurate profile of the donor's blood, particularly regarding the hemoglobin level of the donor. For example, during donation, the loss of blood volume in the donor is compensated by plasma. This compensation by plasma typically lowers the hematocrit of the donor's blood. If the sample is taken after donation, the donor hematocrit may be lower (by possibly as much as 0.5g/dL) than it otherwise would be if the sample is collected prior to donation.

The present invention provides additional advantages, whether used for pre-donation or post-donation sampling. One advantage is the reduced risk of tubing or donor vein collapse as described above. Container 42 acts as a buffer between the sampling vial and tube or vein. Thus, any suction forces generated by introduction of the vacuum sealed tube will be absorbed by the container 42 and not tube or donor vein.

Of course, there may be other advantages of the present system not discussed herein which will be apparent to those of skill in the art.

The present invention has been described in accordance with the preferred embodiments. However, it will be understood that minor variations to the embodiments shown herein may be made without departing from the present invention which is specifically set forth in the appended claims.

What is claimed is:

1. A blood sampling system comprising:
   a container for receiving a biological fluid comprising a pair of oppositely facing walls joined together to define an interior chamber, an inlet port communicating with said interior chamber and an outlet port communicating with said interior chamber opposite said inlet port;
   a tubing segment defining a fluid flow path, said tubing segment communicating with said outlet port and extending substantially into said interior chamber; and
   a sample vial holder attached to said outlet port and in flow communication with said flow path of said tubing segment.

2. The system of claim 1 wherein said holder comprises a first end, a second open end and a body portion defining an interior pocket between said first and second ends, wherein said first end is attached to said outlet port to establish flow communication between said holder and said container interior.

3. The system of claim 2 wherein said holder comprises a piercing member disposed within said interior pocket.

4. The system of claim 1 wherein said holder comprises a generally cylindrical body portion.

5. The system of claim 2 wherein said holder comprises at least one pair of oppositely facing flexible walls comprising said body portion and an openable and closable interior pocket.

6. The system of claim 5 wherein said holder comprises pinching tabs between said flexible walls.

7. The system of claim 3 wherein said holder comprises positioning prongs disposed within the interior pocket of said body portion on either side of said piercing member.

8. The system of claim 6 wherein said holder comprises pinching tabs near said second open end.

9. A disposable blood processing set comprising:
   a first container adapted for receiving blood directly from a donor;
   a vein access device;
   a first tubing segment defining a first flow path between said container and said access device;
   a second container adapted for receiving blood directly from a donor, said second container including an interior chamber, an inlet port, an outlet port and a tubing communicating with said outlet port and extending substantially into the interior chamber;
   a second tubing segment defining an openable flow path between said second container and said access device.

10. The disposable processing set of claim 9 wherein said second tubing segment is joined to said first tubing segment at a junction.

11. The disposable processing set of claim 9 comprising an openable barrier disposed within said second tubing segment.

12. The disposable processing set of claim 9 comprising a holder connected to said outlet port and communicating with said second container interior chamber.

13. The disposable processing set of claim 9 wherein said second container comprises a generally circular fluid receiving chamber.

* * * * *